United States Patent
Phillips (10) Patent No.: US 8,500,806 B1
(45) Date of Patent: Aug. 6, 2013

(54) ACCOMMODATING INTRAOCULAR LENS

(76) Inventor: Andrew F. Phillips, La Canada, CA (US)

( * ) Notice: Subject to any disclaimer, the term of this patent is extended or adjusted under 35 U.S.C. 154(b) by 16 days.

(21) Appl. No.: 13/362,348

(22) Filed: Jan. 31, 2012

(51) Int. Cl.
 *A61F 2/16* (2006.01)
(52) U.S. Cl.
 USPC ....... 623/6.37; 623/6.22; 623/6.27; 623/6.34; 623/6.45; 623/6.56
(58) Field of Classification Search
 USPC .................. 623/6.37, 6.13, 6.22, 6.27, 6.34, 623/6.45, 6.46, 6.5, 6, 56, 58, 62
 See application file for complete search history.

(56) References Cited

U.S. PATENT DOCUMENTS

| | | |
|---|---|---|
| 4,304,012 A | 12/1981 | Richard |
| 4,373,218 A | 2/1983 | Schachar |
| 4,409,691 A | 10/1983 | Levy |
| 4,463,457 A | 8/1984 | Kelman |
| 4,527,294 A | 7/1985 | Heslin |
| 4,534,069 A | 8/1985 | Kelman |
| 4,575,373 A | 3/1986 | Johnson |
| 4,575,878 A | 3/1986 | Dubroff |
| 4,586,930 A | 5/1986 | Kelman |
| 4,666,446 A | 5/1987 | Koziol et al. |
| 4,685,922 A | 8/1987 | Peyman |
| 4,693,717 A | 9/1987 | Michelson |
| 4,718,904 A | 1/1988 | Thornton |
| 4,781,719 A | 11/1988 | Kelman |
| 4,842,601 A | 6/1989 | Smith |
| 4,888,012 A | 12/1989 | Horn et al. |
| 4,888,015 A | 12/1989 | Domino |
| 4,892,543 A | 1/1990 | Turley |
| 4,932,966 A | 6/1990 | Christie et al. |
| 4,994,082 A | 2/1991 | Richards |
| 5,026,393 A | 6/1991 | Mackool |
| 5,108,429 A | 4/1992 | Wiley et al. |
| 5,282,851 A | 2/1994 | Jacob-LaBarre |
| 5,288,293 A | 2/1994 | O'Donnell, Jr. |
| 5,376,115 A | 12/1994 | Jansen |
| 5,476,514 A | 12/1995 | Cumming |
| 5,496,366 A | 3/1996 | Cumming |
| 5,549,668 A * | 8/1996 | O'Donnell, Jr. ............. 623/6.22 |
| 5,571,177 A | 11/1996 | Deacon et al. |
| 5,607,472 A | 3/1997 | Thompson |
| 5,728,156 A | 3/1998 | Gupta et al. |
| 5,769,890 A | 6/1998 | McDonald |
| 6,027,531 A | 2/2000 | Tassignon |
| 6,051,024 A | 4/2000 | Cumming |
| 6,117,171 A | 9/2000 | Skottun |
| 6,197,059 B1 | 3/2001 | Cumming |
| 6,200,342 B1 | 3/2001 | Tassignon |
| 6,217,612 B1 | 4/2001 | Woods |

(Continued)

*Primary Examiner* — Paul Prebilic
(74) *Attorney, Agent, or Firm* — Gordon & Jacobson, PC (57) ABSTRACT

An intraocular lens has a polymeric optic defined by a harder posterior layer and a softer anterior layer. Haptics having a fulcrum attached to the posterior layer and a resistance arm attached to the anterior layer are provided. A bias is provided to the haptic to rotate the haptics about the fulcrum and cause the resistance arm to deform the softer anterior layer about the harder posterior layer to increase the optical power of the lens. As the haptic rotates, it axially displaces the optic anteriorly to additionally increase the optical power. The optical power is adjustable in response to stresses induced by the eye. The haptics are subject to a pre-bias that urges the haptics to rotate or bend about the fulcrum. Temporary restraints are provided to the haptics to retain a stressed shape of the lens against the bias during a post-implantation healing period.

30 Claims, 4 Drawing Sheets

U.S. PATENT DOCUMENTS

| | | | |
|---|---|---|---|
| 6,231,603 B1 | 5/2001 | Lang et al. | |
| 6,261,321 B1 | 7/2001 | Kellan | |
| 6,299,641 B1 | 10/2001 | Woods | |
| 6,413,277 B1 | 7/2002 | Neuhann | |
| 6,443,984 B1 | 9/2002 | Jahn et al. | |
| 6,494,911 B2 | 12/2002 | Cumming | |
| 6,517,577 B1* | 2/2003 | Callahan et al. | 623/6.49 |
| 6,599,317 B1* | 7/2003 | Weinschenk et al. | 623/6.34 |
| 6,660,035 B1 | 12/2003 | Lang et al. | |
| 6,899,732 B2 | 5/2005 | Zadno-Azizi et al. | |
| 7,018,410 B1 | 3/2006 | Vazeen | |
| 7,220,279 B2 | 5/2007 | Nun | |
| 7,601,169 B2 | 10/2009 | Phillips | |
| 7,815,678 B2 | 10/2010 | Ben Nun | |
| 7,842,087 B2 | 11/2010 | Ben Nun | |
| 7,857,850 B2 | 12/2010 | Mentak et al. | |
| 7,998,199 B2 | 8/2011 | Ben Nun | |
| 8,034,106 B2 | 10/2011 | Mentak et al. | |
| 2002/0133228 A1 | 9/2002 | Sarver | |
| 2002/0188351 A1* | 12/2002 | Laguette | 623/6.24 |
| 2003/0060878 A1 | 3/2003 | Shadduck | |
| 2003/0109926 A1* | 6/2003 | Portney | 623/6.37 |
| 2003/0135271 A1 | 7/2003 | Bandhauer | |
| 2003/0187504 A1 | 10/2003 | Weinschenk et al. | |
| 2004/0082993 A1* | 4/2004 | Woods | 623/6.28 |
| 2005/0021139 A1* | 1/2005 | Shadduck | 623/6.35 |
| 2007/0100445 A1* | 5/2007 | Shadduck | 623/6.37 |
| 2010/0036488 A1* | 2/2010 | de Juan et al. | 623/5.16 |

\* cited by examiner

ACCOMMODATING INTRAOCULAR LENS

BACKGROUND OF THE INVENTION

1. Field of the Invention

This invention relates broadly to ophthalmic implants. More particularly, this invention relates to intraocular lenses which are focusable and allow for accommodation for near vision.

2. State of the Art

Figure 1:
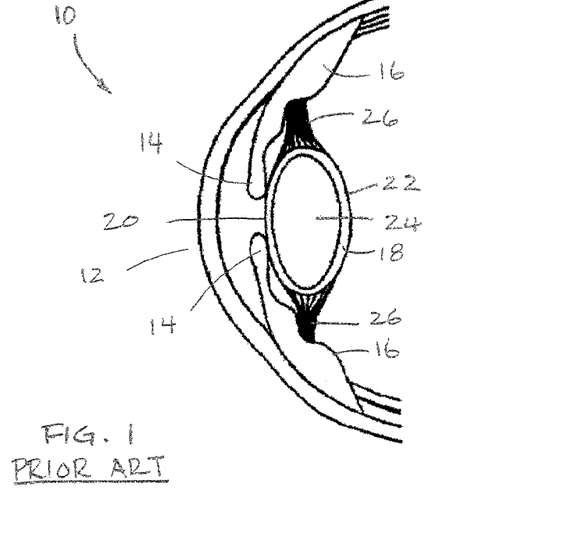
FIG. 1 is a diagrammatic view of a cross-section of a normal eye.

Referring to FIG. 1, the human eye 10 generally comprises a cornea 12, an iris 14, a ciliary body (muscle) 16, a capsular bag 18 having an anterior wall 20 and a posterior wall 22, and a natural crystalline lens 24 contained with the walls of the capsular bag. The capsular bag 18 is connected to the ciliary body 16 by means of a plurality of zonules 26 which are strands or fibers. The ciliary body 16 surrounds the capsular bag 18 and lens 24, defining an open space, the diameter of which depends upon the state (relaxed or contracted) of the ciliary body 16.

When the ciliary body 16 relaxes, the diameter of the opening increases, and the zonules 26 are pulled taut and exert a tensile force on the anterior and posterior walls 20, 22 of the capsular bag 18, tending to flatten it. As a consequence, the lens 24 is also flattened, thereby undergoing a decrease in focusing power. This is the condition for normal distance viewing. Thus, the emmetropic human eye is naturally focused on distant objects.

Through a process termed accommodation, the human eye can increase its focusing power and bring into focus objects at near. Accommodation is enabled by a change in shape of the lens 24. More particularly, when the ciliary body 16 contracts, the diameter of the opening is decreased thereby causing a compensatory relaxation of the zonules 26. This in turn removes or decreases the tension on the capsular bag 18, and allows the lens 24 to assume a more rounded or spherical shape. This rounded shape increases the focal power of the lens such that the lens focuses on objects at near.

As such, the process of accommodation is made more efficient by the interplay between stresses in the ciliary body and the lens. When the ciliary body relaxes and reduces its internal stress, there is a compensatory transfer of this stress into the body of the lens, which is then stretched away from its globular relaxed state into a more stressed elongated conformation for distance viewing. The opposite happens as accommodation occurs for near vision, where the stress is transferred from the elongated lens into the contracted ciliary body.

Figure 2:
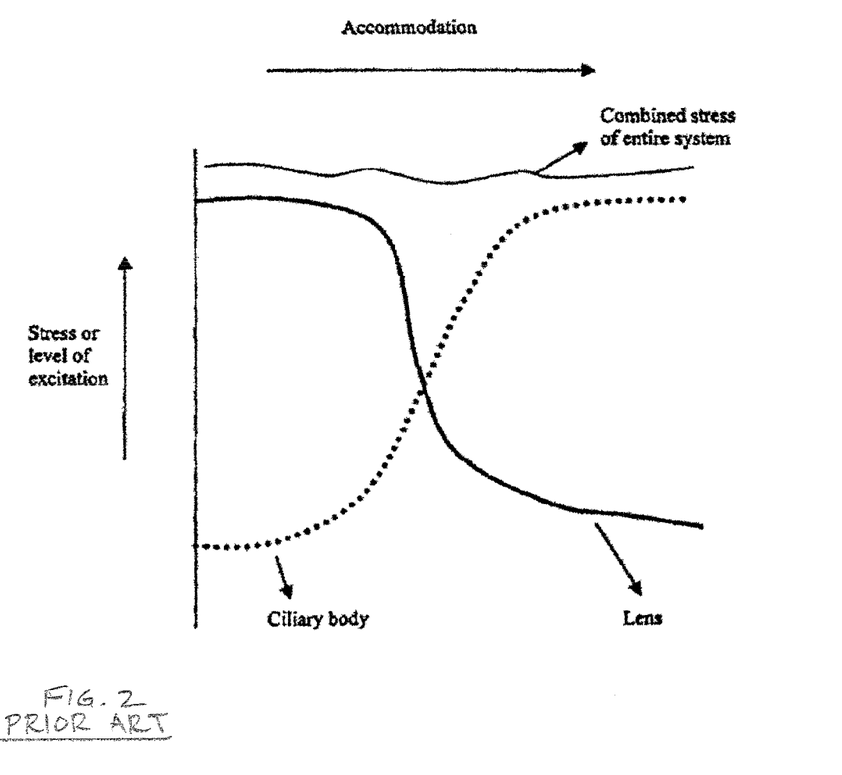
FIG. 2 is a graph of the stresses on the ciliary body-crystalline lens system of the eye in a continuum of states between distance vision and full accommodation.

In this sense, referring to FIG. 2, there is conservation of potential energy (as measured by the stress or level of excitation) between the ciliary body and the crystalline lens from the point of complete ciliary body relaxation for distance vision through a continuum of states leading to full accommodation of the lens.

As humans age, there is a general loss of ability to accommodate, termed "presbyopia", which eventually leaves the eye unable to focus on near objects. In addition, when cataract surgery is performed and the natural crystalline lens is replaced by an artificial intraocular lens, there is generally a complete loss of the ability to accommodate. This occurs because the active muscular process of accommodation involving the ciliary body is not translated into a change in focusing power of the implanted artificial intraocular lens.

There have been numerous attempts to achieve at least some useful degree of accommodation with an implanted intraocular lens which, for various reasons, fall short of being satisfactory. In U.S. Pat. No. 4,666,446 to Koziol et al., there is shown an intraocular lens having a complex shape for achieving a bi-focal result. The lens is held in place within the eye by haptics which are attached to the ciliary body. However, the implant requires the patient to wear spectacles for proper functioning. Another device shown in U.S. Pat. No. 4,994,082 to Richards et al., also utilizes a lens having regions of different focus, or a pair of compound lenses, which are held in place by haptics attached to the ciliary body. In this arrangement, contraction and relaxation of the ciliary muscle causes the haptics to move the lens or lenses, thereby altering the effective focal length. There are numerous other patented arrangements which utilize haptics connected to the ciliary body, or are otherwise coupled thereto, such as are shown in U.S. Pat. No. 4,932,966 to Christie et al., U.S. Pat. No. 4,888,012 to Horne et al. and U.S. Pat. No. 4,892,543 to Turley, and rely upon the ciliary muscle to achieve the desired alteration in lens focus.

In any arrangement that is connected to the ciliary body, by haptic connection or otherwise, extensive erosion, scarring, and distortion of the ciliary body usually results. Such scarring and distortion leads to a disruption of the local architecture of the ciliary body and thus causes failure of the small forces to be transmitted to the intraocular lens. Thus, for a successful long-term implant, connection and fixation to the ciliary body is to be avoided if at all possible.

In U.S. Pat. No. 4,842,601 to Smith, there is shown an accommodating intraocular lens that is implanted into and floats within the capsular bag. The lens comprises front and rear flexible walls joined at their edges, which bear against the anterior and posterior inner surfaces of the capsular bag. Thus, when the zonules exert a tensional pull on the circumference of the capsular bag, the bag, and hence the intraocular lens, is flattened, thereby changing the effective power of refraction of the lens. The implantation procedure requires that the capsular bag be intact and undamaged and that the lens itself be dimensioned to remain in place within the bag without attachment thereto. Additionally, the lens must be assembled within the capsular bag and biasing means for imparting an initial shape to the lens must be activated within the capsular bag. Such an implantation is technically quite difficult and risks damaging the capsular bag, inasmuch as most of the operations involved take place with tools which invade the bag. In addition, the Smith arrangement relies upon pressure from the anterior and posterior walls of the capsular bag to deform the lens, which requires that the lens be extremely resilient and deformable. However, the more resilient and soft the lens elements, the more difficult assembly within the capsular bag becomes. Furthermore, fibrosis and stiffening of the capsular remnants following cataract surgery may make this approach problematic.

U.S. Pat. No. 6,197,059 to Cumming and U.S. Pat. No. 6,231,603 to Lang each disclose an intraocular lens design where the configuration of a hinged lens support ostensibly allows the intraocular lens to change axial position in response to accommodation and thus change effective optical power. U.S. Pat. No. 6,299,641 to Woods describes another intraocular lens that also increases effective focusing power as a result of a change in axial position during accommodation. In each of these intraocular lenses, a shift in axial position and an increase in distance from the retina results in a relative increase in focusing power. All lenses that depend upon a shift in the axial position of the lens to achieve some degree of accommodation are limited by the amount of excursion possible during accommodation.

U.S. Pat. No. 5,607,472 to Thompson describes a dual-lens design. Prior to implantation, the lens is stressed into a non-accommodative state with a gel forced into a circumferential expansion channel about the lens. At implantation, the surgeon must create a substantially perfectly round capsullorrhexis, and insert the lens therethrough. A ledge adjacent to the anterior flexible lens is then bonded 360° around (at the opening of the capsulorrhexis) by the surgeon to the anterior capsule to secure the lens in place. This approach has numerous drawbacks, a few of which follow. First, several aspects of the procedure are substantially difficult and not within the technical skill level of many eye surgeons. For example, creation of the desired round capsullorrhexis within the stated tolerance required is particularly difficult. Second, the bonding "ledge" may disrupt the optical image produced by the adjacent optic. Third, intraocular bonding requires a high degree of skill, and may fail if the capsullorrhexis is not 360° round. Fourth, the proposed method invites cautionary speculation as to the result should the glue fail to hold the lens in position in entirety or over a sectional region. Fifth, it is well known that after lens implantation surgery the capsular bag, upon healing, shrinks. Such shrinking can distort a lens glued to the bag in a pre-shrunk state, especially since the lens is permanently affixed to a structure which is not yet in equilibrium. Sixth, Thompson fails to provide a teaching as to how or when to release the gel from the expansion channel; i.e., remove the stress from the lens. If the gel is not removed, the lens will not accommodate. If the gel is removed during the procedure, the lens is only in a rounded non-stressed shape during adhesion to the capsule, and it is believed that the lens will fail to interact with the ciliary body as required to provide the desired accommodation as the capsular bag may change shape in the post-operative period. If the gel is removed after the procedure, it is ostensibly via an additional invasive surgical procedure. In view of these problems, it is doubtful that the lens system disclosed by Thompson can be successfully employed.

Co-owned U.S. Pat. No. 7,601,169 to Phillips describes an intraocular lens for placement within the capsular bag. The lens includes an optic portion and a surrounding peripheral portion. A bias element is provided to anteriorly vault the optic portion relative to the peripheral portion. A restraint is provided to counter the bias element, and constrain the lens in stressed relatively planar configuration during surgical implantation and a healing period during which the eye is maintained under cycloplegia and the peripheral portion and capsular bag are permitted to naturally fuse together. Then, post-healing, the restraint is removed permitting the bias element to vault the optic portion anteriorly into a non-stressed state such that the optic portion is at an increased distance from the retina relative to the stressed state and has a resulting increased optical power, and wherein the optical power of the lens is adjustable in response to stresses induced by the eye. While significant advantage is provided by the system, limitations in optical power remain from the system.

U.S. Pat. No. 8,034,106 to Mentak describes an intraocular lens retained outside the lens capsule in the posterior chamber. The lens has haptics coupled to the ciliary body. The optic of the lens includes an encapsulation of two immiscible liquids in contact with other and defining a meniscus at their interface. Alternatively, two miscible liquids are encapsulated and separated by an optically transparent film at their meniscus. Forces from the ciliary body are transmitted through the haptics to the interface of the liquids to alter the curvature of the meniscus, and thus alter the accommodating power of the lens. While Mentak considers it an advantage, it may also be considered a drawback that the Mentak lens uses two liquids within the optic of the lens. Should the lens leak such liquid, there is serious concern with respect to the impairment and damage that may be result. In addition, it is possible that over time the liquids may migrate out of the lens, causing ocular damage or changing the optical power, or the liquids may crystallize also leading to vision impairment.

Thus, the prior art discloses numerous concepts for accommodating intraocular lenses. However, none are capable of providing an accommodating implant which does not, in one way or another, present technical barriers or potential serious consequences upon failure of the device or provide an system to which their may be improvement.

SUMMARY OF THE INVENTION

An intraocular lens (IOL) according to the invention permits accommodation through two different mechanisms. The IOL includes an optic and haptic levers. The optic has an anterior surface and a posterior surface and is defined by a first polymeric optic layer and a second optic polymeric layer positioned on the first optic layer. The first polymeric optic layer has a first durometer, an anterior surface, and a posterior surface that defines the posterior surface of the optic. The posterior surface of the first layer has a generally spherical curvature, and the anterior surface of the first layer has an outer portion with a first spherical curvature, and a smaller diametered central portion with a steeper shape, preferably of a second spherical curvature of a lesser radius of curvature than the first spherical curvature. The second polymeric optic layer is relatively softer, with a second durometer lower than the first durometer, an anterior surface with a generally spherical curvature, and a posterior surface that is provided flush against anterior surface of the first layer.

The haptic levers can alter the axial position of the optic within the posterior chamber and deform the second optic layer, each operating to change the optical power of the lens. The haptic levers include a fulcrum attached at the periphery of the first optic layer, a resistance arm coupled to the anterior surface of the second optic layer, and a force arm haptic which engages within the capsular bag. When a force is applied to the haptic levers to cause relatively posterior bending or rotation of the haptic levers relative to the optic, the haptic levers are bent or rotated relative to the first layer, and the following two mechanism are effected to increase the optical power of the IOL. First, as the levers rotate about the fulcrums, the resistance arms stretch at least the anterior surface of the second optic layer. This results in deformation of the second optic layer as the second optic layer bends about the smaller diameter central portion on the anterior surface of the first optic layer to thereby decrease its radius of curvature (steepen the curvature) and consequently increase the central optical power of the lens. Second, with the force arms fixed in the edges of the capsular bag, as the levers bend or rotate about the fulcrums, the entire optic is axially displaced anteriorly to increase the optical power of the lens. This state of increased power permits accommodation.

For the lens to function optimally in accommodation, the haptic levers are subject to a pre-bias such that the levers are naturally biased or otherwise urged to rotate or bend about the fulcrums to stretch at least the anterior surface of the second optic layer and to anteriorly displace the optic relative to the free ends of the force arms. Such pre-bias is preferably applied by integration of a bias element at the haptic-optic junction. Such bias element may comprise a resilient polymer hinge and may be integrated as a periphery of the first optic layer.

When the IOL is held by the optical system or otherwise with the haptic levers and optic of the IOL in a more planar configuration, the force of the bias element must be overcome. The lens is therefore in a stressed state, but the anterior curvature of the lens is flatter and of a lower power suitable for non-accommodative vision.

A restraining element is preferably provided to the IOL for temporarily retaining the IOL in a stressed, planar, non-accommodating configuration during implantation and a post-operative period. The retraining element may comprise a dissolvable bioabsorbable material such that the element automatically releases the optic after a post-operative period, or may be released under the control of an eye surgeon, preferably via a non-surgically invasive means such as via a laser or a chemical agent added to the eye.

Generally, the method for implanting the intraocular lens includes (a) inducing cycloplegia; (b) providing the intraocular lens having an optic portion and haptic levers and having an as manufactured inherent bias induced between the optic portion and haptic levers, the intraocular lens being held in a stressed, planar, non-accommodating state by a restraining means such that the intraocular lens has a lower optical power relative to an accommodating non-stressed state of the lens; (c) inserting the stressed state intraocular lens into a capsular bag of the eye; (d) maintaining cycloplegia until the capsular bag physiologically affixes to the intraocular lens; and (e) releasing the restraining means to permit the intraocular lens to move from the stressed state into the non-stressed state in which the intraocular lens has an increased optical power, and wherein the optical power of the intraocular lens is reversibly adjustable in response to stresses induced by the eye such that the lens can accommodate.

More particularly, according to a preferred method of implantation, the ciliary body muscle is pharmacologically induced into a relaxed stated (cycloplegia), a capsulorrhexis is performed on the lens capsule, and the natural lens is removed from the capsule. The prosthetic lens is then placed within the lens capsule. According to a preferred aspect of the invention, the ciliary body is maintained in the relaxed state for the duration of the time required for the capsule to naturally heal and shrink about the lens; i.e., possibly for several weeks. After healing has occurred, the restraining element automatically or under surgeon control releases the lens from the stressed state. The ciliary body and lens may then interact in a manner substantially similar to the physiological interaction between the ciliary body and a healthy natural crystalline lens.

Alternatively, a fully relaxed lens (i.e., without restraining element) can be coupled to a fully stressed and contracted ciliary body.

The intraocular lens of the invention is compatible with modern cataract surgery techniques and allows for large increases in optical power of the implanted lens. Unlike other proposed accommodating intraocular lens systems, the lens utilizes a change in shape in addition to axial displacement of the lens. In addition, given the fully polymerized materials of the lens, it is safe to use, eliminating various factors from the prior art that can lead to tissue irritation and damage and vision impairment.

Additional objects and advantages of the invention will become apparent to those skilled in the art upon reference to the detailed description taken in conjunction with the provided figures.

BRIEF DESCRIPTION OF THE DRAWINGS

Prior Art

Prior Art

DETAILED DESCRIPTION OF THE PREFERRED EMBODIMENTS

Figure 3:
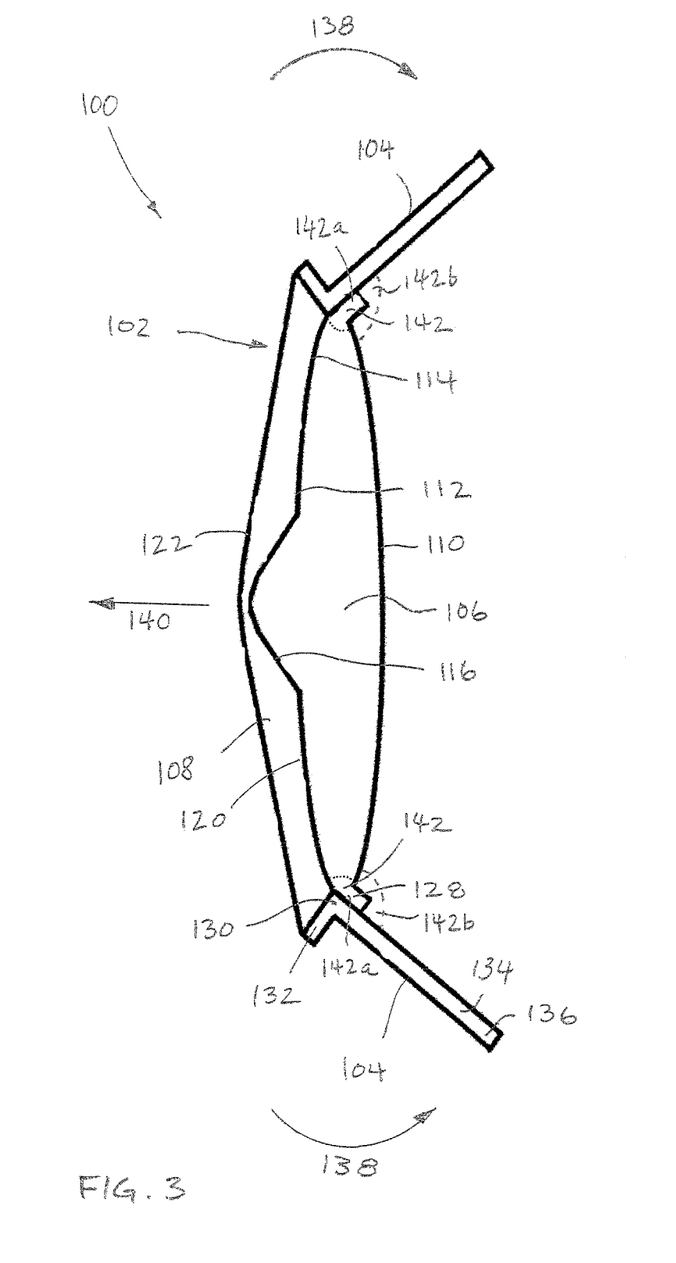
FIG. 3 is a schematic view of an intraocular lens according to the invention in a non-stressed, accommodating configuration.

Turning now to FIG. 3, an intraocular lens (IOL) 100 according to the invention is shown. The IOL 100 includes an optic 102 for focusing light and one or more haptic levers 104. The optic 102 has an overall diameter preferably approximately 4±2 mm, and most preferably 4.75 mm. The optic 102 is defined by a posterior first polymeric optic layer 106 and an anterior second optic polymeric layer 108 positioned on the first optic layer. The posterior first optic layer 106 defines a posterior surface of the optic, and the anterior second optic layer 108 defines an anterior surface of the optic. The first polymeric optic layer 106 is manufactured from a fully-polymerized optically transparent material, preferably a silicone, and has a first durometer preferably in the range of 30 to 60 Shore D. The first optic layer has a posterior surface 110 and an anterior surface 112. The posterior surface 110 of the first optic layer has a generally spherical curvature, and the anterior surface 112 of the first optic layer has a peripheral portion 114 approximating the overall optic diameter and having a first spherical curvature, and a smaller diameter steeper central portion 116, approximately 3±1 mm, preferably having a second spherical curvature of lesser radius of curvature than the first spherical curvature. Alternatively, the steeper central portion may be defined by a cone or a conical or frustoconical section. As yet another alternative, the steeper central portion may be defined by another shape, including an aspherical curve, a square edge, or a catenary. The second optic layer 108 has a posterior surface 120 that is bonded flush against the anterior surface 112 of the first optic layer 106 and an anterior surface 122 with a generally spherical curvature. The second optic layer 108 is made from a fully-polymerized optically transparent material, preferably a silicone, with a second durometer lower than the first durometer and preferably not exceeding 20 Shore D. The second optic layer preferably has a maximum thickness of 80-750μ.

As discussed in more detail below, when the lens 100 is implanted in the capsular bag, forces from the ciliary body of the eye act through the capsular bag and on the one or more haptic levers 104 to (1) alter the axial position of the optic 102 within the posterior chamber of the eye and (2) alter the shape of the second optic layer 108, each of which operates to change the optical power of the lens 100. The haptic levers 104 are stated to be 'one or more' as such may comprise a single ring-shaped lever completely or substantially encircling the periphery of the optic 100, or may comprise a plurality of haptic levers in a preferably evenly radially spaced apart distribution about the periphery of the optic. In the illustrated embodiment, two haptic levers 104 are shown in diametric opposition. However, where a plurality of haptic levers are provided, it is appreciated that two, three, four or more haptic levers can be preferably evenly displaced about the periphery of the optic.

The haptic levers 104 include a fulcrum 130 attached at a peripheral portion 128 (either at one or both of the anterior or posterior surfaces thereof or at the junction of the anterior and posterior surfaces) of the first optic layer 106, a resistance arm 132 coupled to the periphery of the anterior surface 122 of the second optic layer 108, and a force arm 134 having a free 136 end which is adapted to engage the capsular bag near the ciliary body. The haptic levers 104 are also made from a polymer, and more preferably from the same polymer with same hardness/softness as the first optic layer 106. The resistance arms 132 are preferably 200-500μ in length, and the force arms 134 are preferably 2.75 mm in length.

When a force is applied to the haptic levers 104 to cause relatively posterior rotation of the haptic levers relative to the optic 102 (in the direction of arrows 138), the haptic levers 104 are rotated relative to the first optic layer 106, and the following two mechanism are effected to increase the optical power of the lens. First, as the haptic levers 104 rotate on the fulcrums 130, the resistance arms 132 stretch at least the anterior surface 122 of the second optic layer 108. This results in deformation of the second optic layer 108 as the second optic layer bends about the smaller diameter central portion 116 on the anterior surface of the first optic layer 106 to thereby decrease its radius of curvature and consequently increase the optical power of the lens 100. Second, with the force arms 134 fixed in the edges of the capsular bag, as the levers 104 rotate about their respective fulcrums 130, the entire optic 102 is axially displaced anteriorly (in the direction of arrow 140) within the posterior chamber to increase the optical power of the lens. This state of increased power permits accommodation.

For the lens to function optimally in accommodation, the haptic levers are preferably subject to a pre-bias such that the levers are naturally urged to rotate or bend about the fulcrum into an approximately 40°±10° angular bend relative to the diameter of the optic to thereby stretch at least the anterior surface of the second optic layer and to anteriorly displace the optic relative to the free ends of the force arms. Such pre-bias is preferably applied by a bias structure 142 at the haptic-optic junction, and may comprise a resilient polymer hinge 142a integrated at the periphery of the first optic layer 106 or may include a separate bias element 142b acting between the posterior first optic layer 106 and the haptic levers 104.

Figure 4:
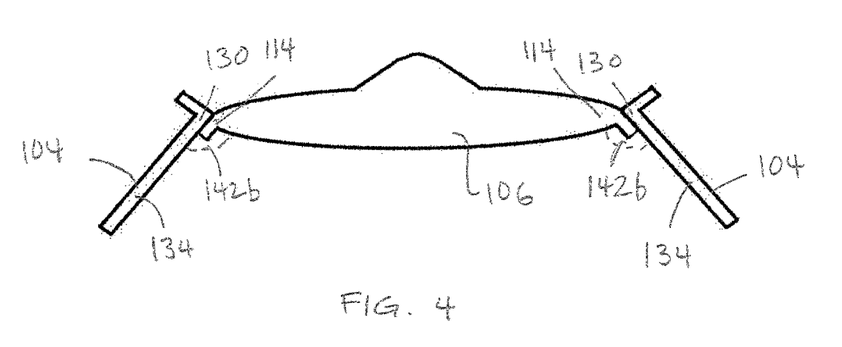
FIGS. 4-6 illustrate manufacture of the intraocular lens of FIG. 3 into a restrained, stressed configuration suitable for implantation.
Figure 5:
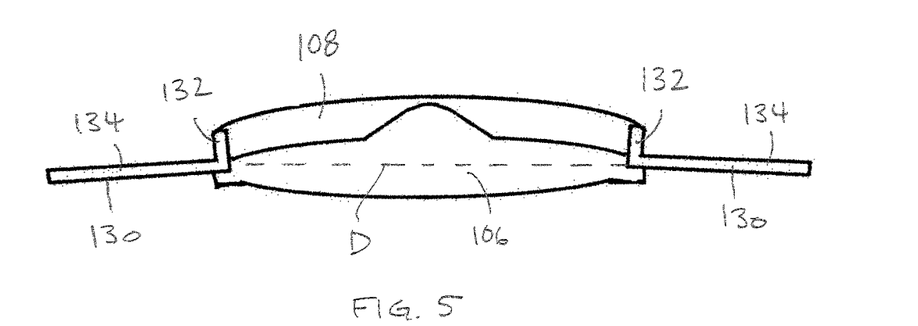
Figure 6:
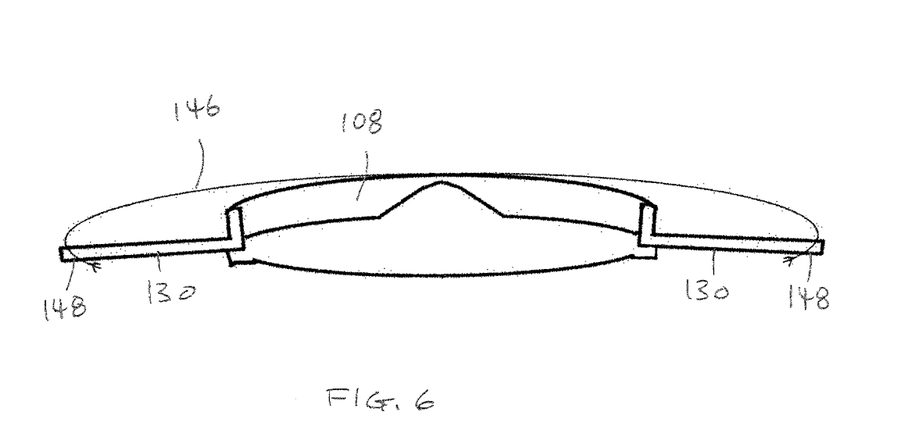

Referring to FIGS. 4 through 6, construction of the optic is preferably as follows. Referring initially to FIG. 4, the posterior first optic layer 106 is molded, preferably with the haptic levers 104 integrated via the molding process. In the first step of the molding process, the fulcrums 130 of the haptic levers 104 are molded into the first optic layer 106 at the periphery 114 of the first optic layer, and the haptic levers 104 are oriented angled posteriorly to the first optic layer to cause the first optic layer 106 to be in a 'vaulted' configuration relative to the force arms 134 of the haptic levers. In an alternative manufacture, the first optic layer 106 and the haptic levers 130 may be integrated at a lesser angle or even in a relatively flat configuration, and a separate bias element 142b is thereafter provided at the haptic-optic junction to bias the construct into the 'vaulted' configuration. Turning now to FIG. 5, once the first optic layer 106 is integrated with the haptic levers 130, the first optic layer 106 and haptic levers 130 are held in a substantially planarized configuration; i.e., with the force arms 134 extending substantially parallel (preferably within ±5°) with the diameter D of the first optic layer 106, and the second optic layer is molded onto the anterior surface of the first optic layer and with the periphery of the second optic layer 108 coupling to the resistance arms 132 of the haptic levers 130.

Referring now to FIG. 6, once the second optic layer 108 has at least substantially cured on the first optic layer 106, a temporary restraint is provided to the optic to maintain the planarized non-accommodative configuration for purposes of implantation and a for a period of post-implantation. Several types of temporary restraints may be used. In one example, the temporary restraint is a suture 146 extending from a first haptic lever 130 across the anterior surface of the second optic layer 108 to a second haptic lever 130. The suture may extend through and be secured at a small hole 148 in the respective haptic levers. The suture is sufficiently taught to maintain the planarized configuration. Alternative restraints includes rigid struts attached to the hatpic levers and extending across the front or back of the optic to maintain the planarized configuration. Yet other alternative restraints include hinge stops at the optic-haptic junction that maintain the planarized configuration by preventing rotation of the haptic levers relative to the optic. Each of the restraints may be made of a dissolvable bioabsorbable material such that the restraint automatically releases the lens from the planarized configuration after a determined post-operative period, or may be released under the control of a eye surgeon, preferably via a non-surgically invasive means such as via a laser or a chemical agent added to the eye.

Figure 7:
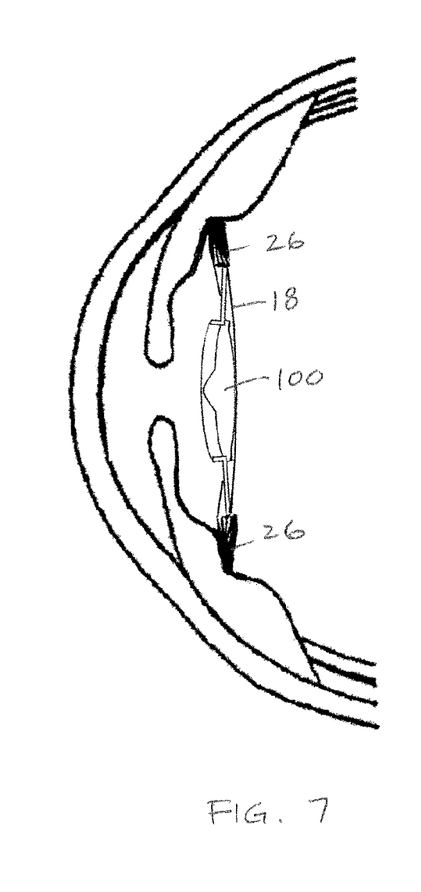
FIG. 7 shows the intraocular lens implanted in a lens capsule of an eye in a stressed, non-accommodative state.
Figure 8:
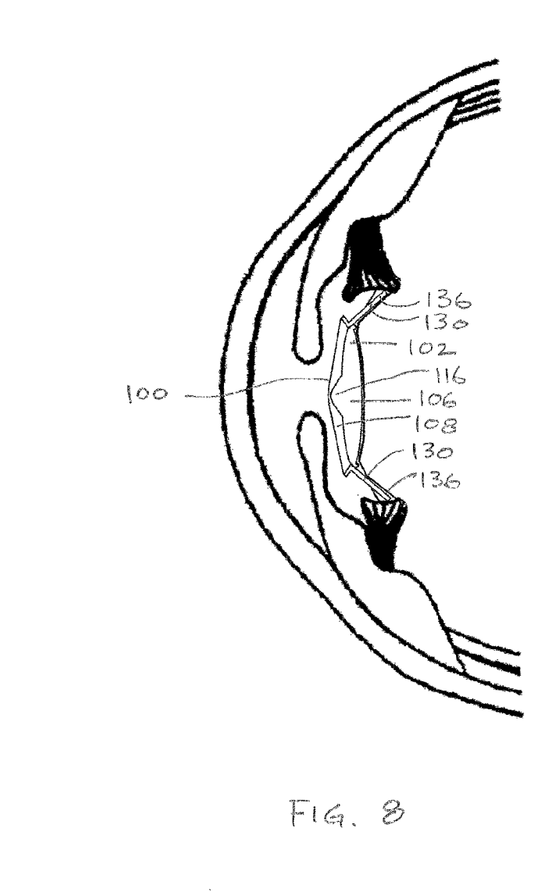
FIG. 8 shows the intraocular lens implanted in a lens capsule of an eye in a non-stressed, accommodative state.

The lens is implanted in the eye as follows. The patient is prepared for cataract surgery in the usual way, including full cycloplegia (paralysis of the ciliary body). Cycloplegia is preferably pharmacologically induced, e.g., through the use of short-acting anticholinergics such as tropicamide or longer-lasting anticholinergics such as atropine. An anterior capsullorrhexis is then performed and the lens material removed. A stressed planarized lens according is selected that has an optic portion that in a stressed-state has a lens power that will leave the patient approximately emmetropic after surgery. The lens is inserted into the empty capsular bag. Cycloplegia is maintained for several weeks (preferably two to four weeks) or long enough to allow the capsular bag to heal and "shrink-wrap" around the stressed lens. This can be accomplished post-operatively through the use of one percent atropine drops twice daily. As the capsular bag shrinks, the anterior and posterior capsular bag walls join to the lens. If the lens includes a restraining element having a dissolvable component, eventually the dissolvable material is lost from the lens, and the lens is unrestrained. If the lens includes a restraining element having a laser-removable component, a surgeon may at a desired time remove the component to place the lens in a unrestrained configuration. If the lens includes a retraining element which must be otherwise removed from the patient, either via a non-surgically invasive procedure or a surgically invasive procedure, the surgeon may at a desired time perform a second eye procedure to remove the component and place the lens in an unrestrained configuration. Regardless of the method used, when the lens is unrestrained (i.e., released from the stressed state) as shown in FIG. 7, and the post-operative cycloplegic medicines are stopped, the lens 100 is initially still maintained in a stressed state due to the inherent stress of the zonules in the non-accommodating eye. When the patient begins accommodating, the zonular stress is reduced and the implanted lens is permitted to reach a more relaxed configuration, as shown in FIG. 8. With release of the zonular stress, the haptics levers 130 reconfigure the lens in accord with the inherent bias of the lens; i.e., to rotate approximately 40°±10° relative to the diameter D of the posterior optic layer 106 causing (1) deformation of the anterior optic layer 108 about the central portion 116 of the posterior optic layer 106 to a cause the anterior optic layer to assume a steeper curvature of greater optical power at the center thereof and (2) anterior axial displacement of the optic 102 relative to the free ends 136 of the haptic levers 130. Theses changes in shape provide the lens with greater dioptic power in the central portion of the optic 102, and thus accommodation for the patient is enabled. As with the natural crystalline lens, the relaxation of the implanted lens, i.e., its permitted movement in accord with its inherent bias, is coupled with a development of strain or stress in the ciliary body during accommodation. Further, when the patient relaxes accommodation, the stress in the ciliary body is reduced, and there is a compensatory gain in stress as the lens is stretched into its planar, non-accommodative shape shown in FIG. 7.

In another embodiment of the implantation of a lens according the invention, a lens of similar design as described above is used except that there is no restraining element on the lens. Temporary cycloplegia is induced, and a capsulorrhexis is performed. The lens is implanted while the ciliary body is in a fully relaxed state. The patient is then fully accommodated (i.e., the ciliary body is placed in a contracted state), preferably through pharmacological agents such as pilocarpine. Once the capsular bag is fully annealed (affixed) to the lens periphery, the pharmacological agent promoting accommodation is stopped. Then, as the ciliary body relaxes, the lens is stretched into an elongated shape having less focusing power. Conversely, as accommodation recurs, the lens returns to it resting shape having greater focusing power.

Alternatively, a fully relaxed lens (i.e., without restraining element) can be coupled to a fully stressed and contracted ciliary body.

The intraocular lens systems described above operates to provide accommodation through a change in shape in and position of the optic resulting from an equilibrium of the anatomical forces and the forces in the lens.

The intraocular lens of the invention is compatible with modern cataract surgery techniques and allows for large increases in optical power of the implanted lens. Unlike other proposed accommodating intraocular lens systems, the lens utilizes a change in shape in addition to axial displacement of the lens. In addition, the fully polymerized silicone materials of the lens are safe to use, eliminating various factors from the prior art, including potential tissue irritation, damage and vision impairment, and significant hurdles from regulatory authorities.

There have been described and illustrated herein embodiments of an intraocular lens. While particular embodiments of the invention have been described, it is not intended that the invention be limited thereto, as it is intended that the invention be as broad in scope as the art will allow and that the specification be read likewise. Thus, while silicone is the preferred material for all components of the lens, it is appreciated that other polymers, such as acrylics can also be used. In addition, particularly where other materials are used, a different range of durometers for each of the first and second optic layers can be used. It will therefore be appreciated by those skilled in the art that yet other modifications could be made to the provided invention without deviating from its spirit and scope as claimed.

What is claimed is:

1. An intraocular lens for replacement of a natural crystalline lens within a capsular bag during eye surgery, the intraocular lens to be positioned anterior to the retina when implanted in the eye, said intraocular lens comprising:
  a) an optic adapted to focus light, said optic having an anterior surface, a posterior surface, and a central portion, said optic comprising,
    i) a polymeric posterior first optic layer having a first durometer, an anterior surface and a posterior surface, said anterior surface having a peripheral portion with a first radius of curvature and a relatively steeper central portion, said posterior surface of said first optic layer defining said posterior surface of said optic, and
    ii) a polymeric anterior second optic layer having a second durometer less than said first durometer, and including a posterior surface, an anterior surface, and central portion, said posterior surface of said second optic layer bonded flush against said anterior surface of said first optic layer, and said anterior surface of said second optic layer defining said anterior surface of said optic;
  b) at least one haptic lever extending from said optic, each said haptic lever including a fulcrum attached to said first optic layer, a resistance arm attached to said second optic layer, and a force arm extending from said optic, wherein when a force is applied to rotate said haptic lever on said fulcrum in a posterior direction relative to said second optic layer,
    i) said resistance arm pulls said second optic layer to deform said second optic layer about said central portion of said first optic layer and steepen a curvature of said anterior surface of said second optic layer, and
    ii) said optic is axially displaced anteriorly relative to said haptic lever;
  c) biasing means for biasing said haptic lever to rotate on said fulcrum into a posterior direction relative to said second optic layer into a non-stressed state; and
  d) a restraining element operating against said biasing means so as to maintain said optic and said at least one haptic lever in a stressed state of relatively greater planarity than said non-stressed state,
    said restraining element being releasable without an invasive surgical procedure after completion of the eye surgery during which said intraocular lens is implanted, and
    when said lens is implanted in the eye an optical power of said lens is adjustable in response to stresses induced by the eye.

2. An intraocular lens according to claim 1, wherein:
said steeper central portion of said anterior surface of said first optic layer has a second radius of curvature smaller than said first radius of curvature.

3. An intraocular lens according to claim 1, wherein:
said first optic layer is made of a first silicone material, and said second optic layer is made of a second silicone material.

4. An intraocular lens according to claim 3, wherein:
said first silicone material has a durometer in the range of 30-60 Shore D, and said second silicone material has a durometer not exceeding 20 Shore D.

5. An intraocular lens according to claim 3, wherein:
said at least one haptic lever is made from a silicone material.

6. An intraocular lens according to claim 5, wherein:
said first optic layer and said at least one haptic lever are made from a same silicone material.

7. An intraocular lens according to claim 1, wherein:
said biasing means is provided at a junction of said optic and said haptic lever.

8. An intraocular lens according to claim 1, wherein:
said biasing means is integrated into a periphery of said posterior optic layer.

9. An intraocular lens according to claim 1, wherein:
said biasing means is a periphery of said posterior optic layer.

10. An intraocular lens according to claim 1, wherein:
said restraining element holds said anterior surface of said optic of said lens at an first curvature, and when the lens is implanted in the eye, is released of said restraining element, and is subject to forces of accommodation, a central portion of said anterior surface of said optic of said lens assumes a second curvature having a reduced radius of curvature.

11. An intraocular lens according to claim 1, wherein:
said restraining element holds said optic of said lens in a first shape having a first diopteric power, and when said lens is implanted in the eye, is released of said restraining element, and is subject to forces of accommodation, a central portion of said anterior portion of said optic of said lens assumes a second shape having a second dioptic diopteric power greater than said first diopteric power.

12. An intraocular lens according to claim 11, wherein said restraining element extends across said anterior surface of said optic.

13. An intraocular lens according to claim 1, wherein:
said restraining element is chemically dissolvable.

14. An intraocular lens according to claim 1, wherein:
said restraining element is laser releasable.

15. An intraocular lens according to claim 1, wherein:
said at least one haptic lever comprises two diametrically opposed haptic levers.

16. An intraocular lens for replacement of a natural crystalline lens within a capsular bag during eye surgery, the intraocular lens to be positioned anterior to the retina when implanted in the eye, said intraocular lens comprising:
 a) an optic adapted to focus light, said optic having an anterior surface, a posterior surface, and a central portion, said optic comprising,
  i) a polymeric posterior first optic layer having a first durometer, an anterior surface and a posterior surface, said anterior surface having a peripheral portion with a first radius of curvature and a relatively steeper central portion, said posterior surface of said first optic layer defining said posterior surface of said optic, and
  ii) a polymeric anterior second optic layer having a second durometer less than said first durometer, and including a posterior surface, an anterior surface, and central portion, said posterior surface of said second optic layer bonded flush against said anterior surface of said first optic layer, and said anterior surface of said second optic layer defining said anterior surface of said optic;
 b) first and second haptic levers each extending from said optic, said haptic levers each including a fulcrum attached to said first optic layer, a resistance arm attached to said second optic layer, and a force arm extending from said optic, wherein when a force is applied to rotate said haptic lever on said fulcrum in a posterior direction relative to said second optic layer,
  i) said resistance arm pulls said second optic layer to deform said second optic layer about said central portion of said first optic layer and steepen a curvature of said anterior surface of said second optic layer, and
  ii) said optic is axially displaced anteriorly relative to said haptic levers;
 c) biasing means for biasing said haptic levers to rotate on said respective fulcrums into a posterior direction relative to said second optic layer to urge said lens into a non-stressed state; and
 d) a releasable restraining element including at least one element extending continuously across said optic from one of said haptic levers across said optic to another of said haptic levers, said restraining element countering said bias between said optic and said haptic levers so as to maintain said lens in a relatively planar stressed-state,
  wherein said restraining element holds said lens in said stressed state, and when said lens is implanted in the eye, upon release of said restraining element, said biasing means (i) urges said optic anteriorly relative to the retina and (ii) causes rotation of said haptic levers relative to said lens to deform said central portion of said anterior second optic layer about said central portion of said anterior surface of said first optic layer, each resulting in increased optical power of said lens, and
  wherein said optical power of said lens is adjustable in response to stresses induced by the eye.

17. An intraocular lens according to claim 16, wherein:
said biasing means is provided at a junction of said optic and said haptic levers.

18. An intraocular lens according to claim 16, wherein:
said biasing means is integrated into said posterior optic layer.

19. An intraocular lens according to claim 18, wherein:
said biasing means is integrated into a periphery of said posterior optic layer.

20. An intraocular lens according to claim 16, wherein:
said biasing means is a periphery of said posterior optic layer.

21. An intraocular lens according to claim 16, wherein:
said restraining element holds said central portion of said anterior surface of said optic of said lens at a first curvature, and
when said lens is implanted in the eye, is released of said restraining element, and is subject to forces of accommodation, said central portion of said anterior surface of said optic lens assumes a second curvature having a smaller radius of curvature than said first curvature.

22. An intraocular lens according to claim 16, wherein:
said restraining element holds said optic of said lens in a first shape in which a central portion of said optic has a first diopteric power, and when said lens is implanted in the eye, is released of said restraining element, and is subject to forces of accommodation, said optic of said lens assumes a second shape in which said central portion of said lens has a second diopteric power greater than said first diopteric power.

23. An intraocular lens according to claim 16, wherein
said restraining element extends across said anterior surface of said optic.

24. An intraocular lens according to claim 16, wherein:
said restraining element is chemically dissolvable.

25. An intraocular lens according to claim 16, wherein:
said restraining element is laser releasable.

26. An intraocular lens according to claim 16, wherein:
said steeper central portion of said anterior surface of said first optic layer has a second radius of curvature smaller than said first radius of curvature.

27. An intraocular lens according to claim 16, wherein:
said steeper central portion of said anterior surface of said first optic layer is defined by a conical section.

28. An intraocular lens according to claim 16, wherein:
said first optic layer is made of a first silicone material, and said second optic layer is made of a second silicone material.

29. An intraocular lens according to claim 28, wherein:
said first silicone material has a durometer in the range of 30-60 Shore D, and said second silicone material has a durometer not exceeding 20 Shore D.

30. An intraocular lens according to claim 28, wherein:
said first optic layer and said first and second haptic levers are made from said first silicone material.

* * * * *